United States Patent [19]

Czernecki et al.

[11] Patent Number: 5,710,371
[45] Date of Patent: Jan. 20, 1998

[54] CONTAINER FOR CALIBRATING FLUIDS, AND DEVICE AND METHOD FOR MEASURING PARAMETERS OF A SAMPLE OF FLUID, AND OXYGEN ELECTRODE THEREFOR

[75] Inventors: Andrzej Czernecki, Warsaw; Andrzej Bylina, Legionowo; Jan Kawiak; Piotr Ohnsorge, both of Warsaw, all of Poland

[73] Assignee: Przedsiebiorstwo Zagraniczne HTL, Warsaw, Poland

[21] Appl. No.: 589,617

[22] Filed: Jan. 22, 1996

[30] Foreign Application Priority Data

Jan. 25, 1995 [PL] Poland ........................ 306960
Sep. 19, 1995 [PL] Poland ........................ 310543

[51] Int. Cl.$^6$ .......................... G01N 27/42; G01N 33/18; G01M 03/04
[52] U.S. Cl. ................ 73/53.01; 73/864.81; 73/864.91; 204/421; 204/433
[58] Field of Search ................ 73/53.01, 864.81, 73/864.82, 864.84, 864.91; 204/421, 422, 433

[56] References Cited

U.S. PATENT DOCUMENTS

3,874,850  4/1975  Sorensen et al. ............... 23/23 B
3,884,640  5/1975  Lock et al. ..................... 23/253 R
3,964,864  6/1976  Dahms ........................... 23/230 B
4,356,722  11/1982 Bunce et al. .................... 73/53
4,696,183  9/1987  Mitsumaki et al. .............. 73/19
4,846,005  7/1989  Bacehowski et al. ............ 73/864.81
4,871,439  10/1989 Enzer et al. .................... 204/401
5,140,845  8/1992  Robbins ......................... 73/19.03
5,325,709  9/1994  Lee ................................ 73/61.43
5,357,781  10/1994 Tikijian ........................... 73/19.1
5,531,096  7/1996  Castor ............................ 73/23.2

*Primary Examiner*—Hezron E. Williams
*Assistant Examiner*—J. David Wiggins
*Attorney, Agent, or Firm*—Micheal D. Bednarek; Kilpatrick Stockton LLP

[57] ABSTRACT

A device for measuring the parameters of a sample of fluid comprising exchangeable containers for calibrating fluids and an oxygen electrode. The device comprising a measuring chamber having at least two measuring channels with measuring electrodes for determining the acid-base equilibrium parallel introduced into the measuring channel of the device and connected with a common electronic system. The exchangeable containers for calibrating fluids each comprising an elastic, impermeable container for gases with an elastic joint for ensuring tightness of the connection between the container and a device. The oxygen electrode comprising an oxygen electrode of a Clark's electrode system with an anode made of an element selected from the VIB group of the periodic system of chemical elements.

10 Claims, 6 Drawing Sheets

CONTAINER FOR CALIBRATING FLUIDS, AND DEVICE AND METHOD FOR MEASURING PARAMETERS OF A SAMPLE OF FLUID, AND OXYGEN ELECTRODE THEREFOR

BACKGROUND OF THE INVENTION

1. Field of the Invention

This invention relates to a container for calibrating fluids and to a device and method for measuring parameters of a sample of fluid, in particular for measuring gas parameters, such as the values of pH, $pCO_2$ and $pO_2$ and the concentrations of Na+, K+ and Cl-ions, in blood and in blood substitutes, and an oxygen electrode for the device.

2. Description of the Related Art

U.S. Pat. No. 3,874,850 discloses a method for performing a blood analysis that comprises introducing a sample of blood into a hydraulic line having measuring devices therein, measuring parameters of the blood sample, such as pH value and the partial pressures of $PCO_2$ and $pO_2$, and then removing the sample of blood from the line. Then, a rinsing fluid is passed through the line before introducing the next sample of blood, and the specified amounts of at least two calibrating fluids with different standard values of pH, $pCO_2$ and $pO_2$ are introduced and passed in succession, in controlled intervals of time, these standard values being determined with the measuring instruments. In this known method, both the measured standard values and the measured values of blood parameters are stored and processed to obtain easy-to-interpret results of blood analysis.

The '850 patent also discloses an automatic blood sample analyzer comprising a hydraulic line having an inlet section for introducing the samples of blood, and a measuring section with instruments for determining at least one parameter of blood, such as electrodes for measuring the values of pH, $pCO_2$ and $pO_2$. This analyzer also comprises containers for rinsing fluids and for calibrating fluids, those containers being connected with the measuring section of the line, and pumping devices for effecting the flow and for removing the samples of blood from the measuring section of the line. Moreover, the analyzer comprises a computerized control system to control the work of pumping devices, to maintain a constant temperature in the containers and in the measuring section of the line, and to convert the standard values and the values of blood parameters determined by the measuring devices into the digital values of those parameters.

European Patent Publication EP 0 012 031 discloses a method for measuring a chemical parameter of a fluid, for example of blood, which comprises placing a determined amount of the examined fluid in a measuring chamber, contacting the fluid with a measuring electrode immersed in the electrolyte solution, and determining the electric potential between the measuring electrode and the reference electrode. As a result, the value of the chemical parameter of the fluid placed in the measuring chamber is obtained.

The EP '031 publication also discloses a device for determining chemical properties of fluids, this device comprising a housing with an upper and a lower surface and with a channel located longitudinally in this housing. This known device possesses a measuring electrode placed along the longitudinal axis of the channel with its terminal being introduced into the channel, and a reference electrode displaced in respect to the measuring electrode. Moreover, this device comprises a measuring chamber which bridges the reference electrode with the measuring electrode, a unit for introducing electrolyte to moisten the electrodes with electrolyte and to establish a standard potential between these electrodes, and a channel suitable for introducing the examined fluid into the terminal of the measuring electrode in order to displace electrolyte from it, whereas the potential established between the electrodes determines the value of a property of the chemically examined fluid.

Further, U.S. Pat. 3,884,640 describes a device for measuring at least two of the following parameters of a fluid: pH, partial pressure of a gas or of gases dissolved in the fluid, concentration of inorganic ions and of hemoglobin, and temperature. This device comprises a vessel with a flow channel for the fluid, this flow channel being equipped with a unit for turbulent flow generation in at least two portions of the channel during measurement of the parameters of the fluid. Moreover, this device possesses at least two units of sensors placed inside the channel in the vicinity of one of the units serving for the turbulent flow generation, and a heat-exchange unit inside the vessel to maintain the desired temperature of the fluid flowing inside the channel and inside the unit of sensors in the vessel.

Moreover, U.S. Pat. No. 4,871,439 discloses an analyzer with a self-calibrating electrode system. This analyzer possesses a measuring chamber containing various electrode systems, and an electronic control and measuring system.

The well-known oxygen electrode, which is used for example in the measurements of the partial $O_2$ pressure in blood, is an electrode based on the so-called Clark's electrode system. It works on the principle of the cathodic reduction of oxygen diffusing from blood across a membrane to electrolyte. Simultaneously, an anodic oxidation reaction takes place. The intensity of the current flowing in the Clark's electrode system is proportional to the partial $O_2$ pressure in blood, and the calibration of the electrodes is normally carried out by taking gas samples with two different and known values of $O_2$ concentration. A typical Clark's electrode system possesses a cathode made of noble metal, such as platinum or gold, and a silver anode, preferably coated with a thin layer of silver chloride.

A drawback of the oxygen electrode based on Clark's electrode system is the disadvantageous phenomenon of silver deposition during the work of the electrode. Silver comes from the anode and is electrolytically deposited on the cathode. This process is due to the flow of an additional current between the anode and the cathode, which is added to the current of oxygen reduction on the cathode. This current varies in time and results in an instability of the total current measured on the electrode, and thus causes an error in the measurement of the partial $O_2$ pressure. Besides, the deposition of silver on the cathode reduces the rate of oxygen reduction and results in nonlinear characteristics of the oxygen electrode. Both these phenomena build up with time and make it necessary to clean the cathode surface periodically by mechanically wearing off the deposited silver layer.

A series of solutions are known to eliminate the deposition of silver onto the cathode of the oxygen electrode. One of these solutions is presented in U.S. Pat. No. 4,486,291, in which a barrier layer for silver ions between the anode and the cathode is used.

SUMMARY OF THE INVENTION

According to one aspect of the present invention, a container for calibrating fluids in a device for measuring parameters of a sample of fluid comprises: an elastic, impermeable container for gases, the container having a connecting element that is a self-tightening elastic joint ensuring tightness of the connection between the container and the device, which remains closed during filling, storing, installing and using the container in the device, wherein the calibrating fluids maintain a constant concentration of saturating gases during the storage, installation and use of the container.

In a further aspect of the present invention, an oxygen electrode for use in a device using the Clark's electrode system for measuring the parameters of a sample of fluid comprises an anode made of an element of the VIB group of the periodic system of elements, preferably selected from such elements as tungsten or molybdenum.

In a further aspect of the present invention, a device for measuring the parameters of a sample of fluid comprises an analyzer and a control unit with a monitor, the analyzer comprising a measuring chamber with measuring electrodes, the chamber being connected with containers for calibrating fluids and for working fluids and into which a sample of the measured fluid, control elements and operating elements to control the operation of the device and to maintain its constant temperature, as well as elements for transforming the results of measurements into the quantities of parameters of the sample of fluid, are introduced, wherein the chamber comprises the exchangeable containers of the calibrating fluids according to the invention. This device for the measurement of the parameters of a sample of fluid also preferably comprises the oxygen electrodes according to the invention.

The device according to the present invention also preferably comprises at least two measuring channels with measuring electrodes in the measuring chamber for measuring the acid-base equilibrium included in the measuring channel of the device and incorporated into the common electronic systems.

In a further aspect of the present invention, a method is provided for measuring the parameters of a sample of fluid, in which the samples of the measured fluid, of the calibrating fluid and of the working fluid are passed through a measuring chamber at specified intervals of time, measurements of the physico-chemical properties of the measured fluid and of the calibrating fluids are performed with the measuring electrodes, and then, on the basis of the results of these measurements, the quantities of the parameters of a sample of fluid are determined. The method also comprising the step of introducing the standard aqueous solutions saturated with gases, as well as the oxygen taken from air, as calibrating fluids for the measuring electrodes in the measuring chamber. These solutions are then divided among at least two measuring channels in the measuring chamber alternatively with the measured sample of fluid and with the working fluids and in accordance with the measuring cycle, each channel comprising the measuring electrodes for determining the acid-base equilibrium, and the results of measurement are recalculated for each measuring channel in the common electronic systems.

An advantage of the solution according to the present invention is the independence of the measured parameters of a sample of fluid from the conditions in external installation, in particular in the cylinders with calibrating gases, because the standard amount of a gas, e.g., of carbon dioxide, remains dissolved in a solution in the exchangeable bags containing the calibrating fluids, and oxygen is taken from air. Moreover, the separation of at least two measuring channels in the measuring chamber makes it possible to change the chamber rapidly in case of any damage, inefficiency of the electrodes or fragments of the measuring channels. The solution according to the invention enhances the reliability of the whole device and accelerates the measurements. It is also advantageous to use the common electronic systems of the present invention for recalculating the results of measurements from each measuring channel in the measuring chamber, and for controlling the hydraulic elements separately in each measuring channel.

An advantage of the oxygen electrode according to the present invention is that the oxygen electrode eliminates the flow of an additional current between the anode and the cathode resulting from the reduction on the cathode of substances deriving from oxidation of the anode, and also eliminates the contamination of the cathode material by these substances. In this way, it is possible to improve significantly the stability of parameters of the oxygen electrode and to eliminate the necessity of a periodic purification of the cathode surface.

BRIEF DESCRIPTION OF THE DRAWINGS

The accompanying drawings, which are incorporated in, and form a part of, the specification, illustrate an embodiment of the present invention and, together with the description, serve to explain the principles of the invention. In the drawings.

DETAILED DESCRIPTION OF THE INVENTION

Reference will now be made in detail to the preferred embodiment of the invention, an example of which is illustrated in the accompanying drawings.

Figure 1:
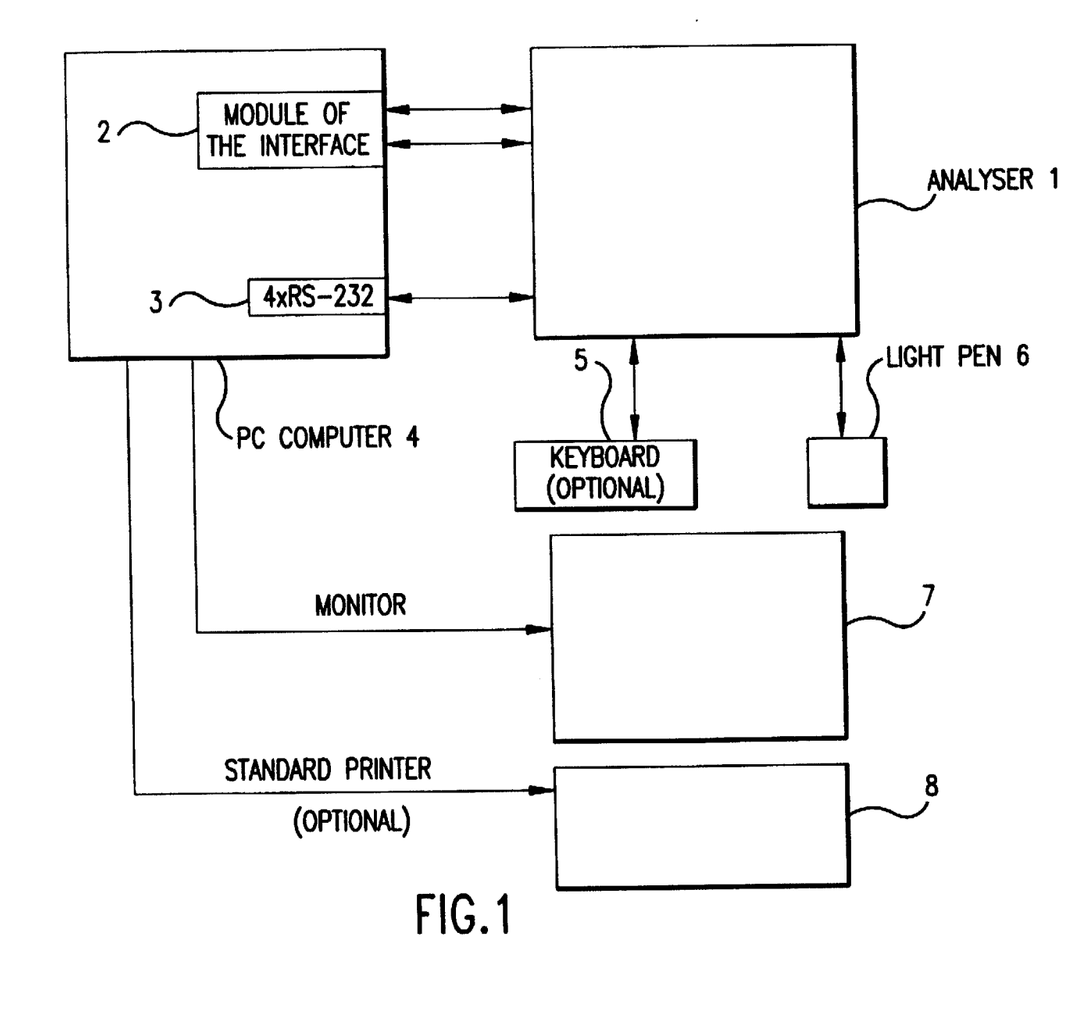
FIG. 1 is a block diagram of a device according to the present invention for measuring the parameters of a sample of fluid.

Referring to FIG. 1, a device for measuring the parameters of a sample of fluid according to the present invention is illustrated in block diagram form. The device comprises an analyzer 1, a control unit 4 connected with the analyzer 1 via an analog-to-digital interface module 2, and an additional interface module 3. The analyzer 1 is connected with a keyboard 5 and a light pen 6, and the control unit 4 is connected with a monitor 7 and a printer 8.

The control unit 4, together with the monitor 7 and with an operating store, a hard disk and a floppy disks drive (these items are not shown in the FIG. 1 diagram) make up a computer. This computer is not placed on the measuring stand and is connected by a cable with the analyzer 1. The monitor 7 serves for visual communication with the user. The monitor 7 is placed in the vicinity of the analyzer 1 and is connected directly with the output of the graphic card of the computer.

The keyboard 5, the use of which is optional, is connected to a socket in the face wall of the analyzer 1. The keyboard 5 serves for recording the alphanumeric data into the data base and into the tests.

The module 2 of the analog-to-digital interface comprises input and output channels in the form of an extending computer cartridge working on a 16-bit bus. The chart recorder communicates directly with the computer via its bus of input-output extension by means of program statements of the processor and of rapid transmissions to the operating store. The chart recorder is connected with the analyzer 1 with measuring and digital cables. The measuring cables comprise wires screened individually for each channel. The module of the additional interface 3 serves for communicating the computer with peripheral equipment and optionally with a head computer.

A light pen 6 serves as a reader of the bar code on the bags with calibrating fluids, on the samples of patient's blood, on the identity card of a medical staff member, and on the patient's card. The light pen 6 connected with the socket on the wall of the analyzer 1 communicates with the computer via an adjusting system either located inside the analyzer 1 or built into the light pen 6. Optionally, instead of the light pen 6, it is possible to use a reader of the bar code with a charge-coupled device CDD reading matrix. The printer 8 is a standard peripheral equipment connected with the Centronix interface in the computer and serves for making text printouts, printouts from the data bases, and so forth.

Figure 2:
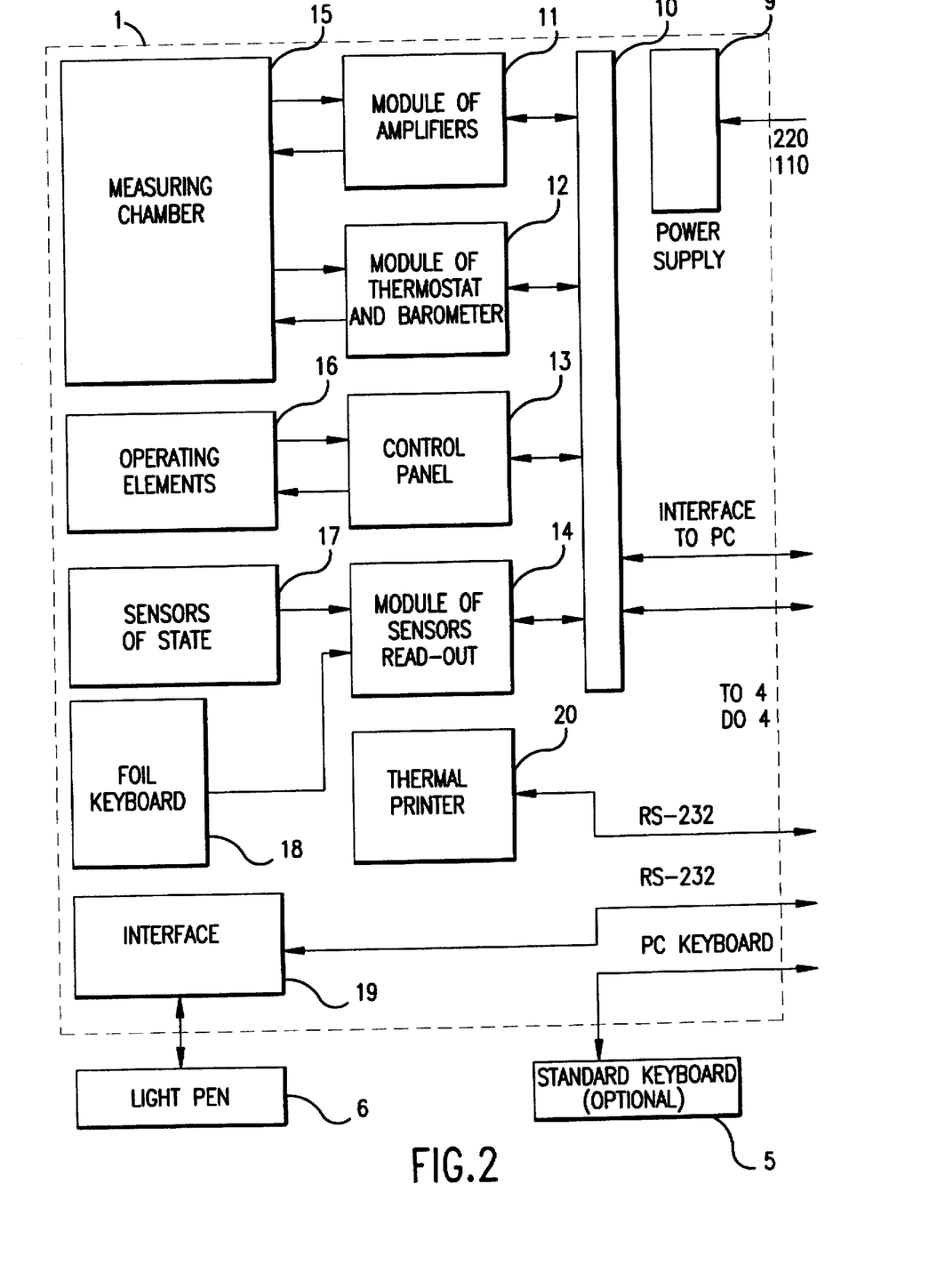
FIG. 2 shows a detailed schematic of the analyzer.

The analyzer 1, as shown in the detailed block scheme in FIG. 2, comprises: a feeder cable 9 delivering all the necessary supply voltages to the sides of the analyzer 1; amplifying modules 11 connected to the common bus 10; a thermostat and barometer module 12; a control panel 13; and a readout of the sensors module 14. The measuring chamber 15 is connected with the amplifying modules 11 and with the thermostat and barometer module 12; the operating elements 16 are connected with the control panel 13; and the sensors of state 17 and the local foil keyboard 18 of the analyzer 1 are connected with the sensors readout module 14. Moreover, the analyzer 1 comprises an interface 19 for connecting the analyzer with the light pen 6, a miniprinter 20, the keyboard 5, the interface 19, the miniprinter 20 and the common bus 10 connected with the control unit 4 of the computer.

The amplifying module 11 comprises a series of analog preamplifiers (not shown) placed near the measuring electrodes in the measuring chamber 15. These preamplifiers are: converters of impedance for signals from the pH electrodes and from the ion-selective electrodes; an amplifier of the signal from the $pCO_2$ electrode; and a current-voltage converter and amplifier of the signal of the $pO_2$ electrode. The amplifying module 11 also comprises a set of analog keys (not shown) for performing auto-tests of the individual amplifiers (zeroing and calibration) and a set of voltage amplifiers with low-pass filters to standardize signals for the analog-to-digital converter.

Electrodes based on the Clark's electrode system are used in the device as oxygen electrodes. These electrodes use an anode made of an element of the VIB group of the periodic system of elements, preferably selected from such elements as tungsten or molybdenum.

The module of thermostat and barometer 12 comprises two independent units. One of them is the unit of the atmospheric pressure sensor with a measuring bridge and a signal amplifier with its output adjusted to readout by an analog-to-digital converter, and the other is an electronic temperature stabilizer in the measuring chamber 15, which is controlled by a temperature sensor placed in the chamber 15 and which has a power output to heating elements. The elements of these units are not shown in the drawings.

As mentioned above, the amplifying modules 11 and the modules of thermostat and barometer 12 are connected with the measuring chamber 15, this measuring chamber 15 being a thermostated block of electrodes made of metal and of a plastic material. The measuring chamber 15 comprises a set of electrodes introduced into the hydraulic system of the analyzer, the electric outlets of the electrodes being connected directly to the amplifying module 11. Block temperature is stabilized by the thermostat and barometer module 12. The heating elements and the temperature sensors (not shown) are placed in this block. The temperature sensors include a first sensor for temperature stabilization, a second sensor for controlling the stabilization system, and a third sensor for directly measuring the sample temperature in the measuring chamber 15.

The control module 13 comprises two-state power amplifiers controlled from the computer for a direct control of the operating elements 16, such as valves, motors and pumps in the hydraulic and mechanical system of the analyzer 1. The control module 13 performs a read-out of the initial state, thereby ensuring the detection of a majority of defects occurring in the operating elements 16, such as short-circuits or burnouts.

The module of sensors read-out 14 comprises two-state systems to read the state of the local foil keyboard 18 of the analyzer 1 and the state of various sensors 17 in the hydraulic and mechanical system of the analyzer 1, such as, for example, the contact and terminal sensors indicating the presence of fluids. The foil keyboard 18 is placed on the front wall of the analyzer 1 casing and serves to control the course of measurement and to introduce numerical data. Further, a miniprinter 20 of the analyzer 1, controlled from the computer, ensures the printout of the results of measurements, calibrations and tests.

Figure 3:
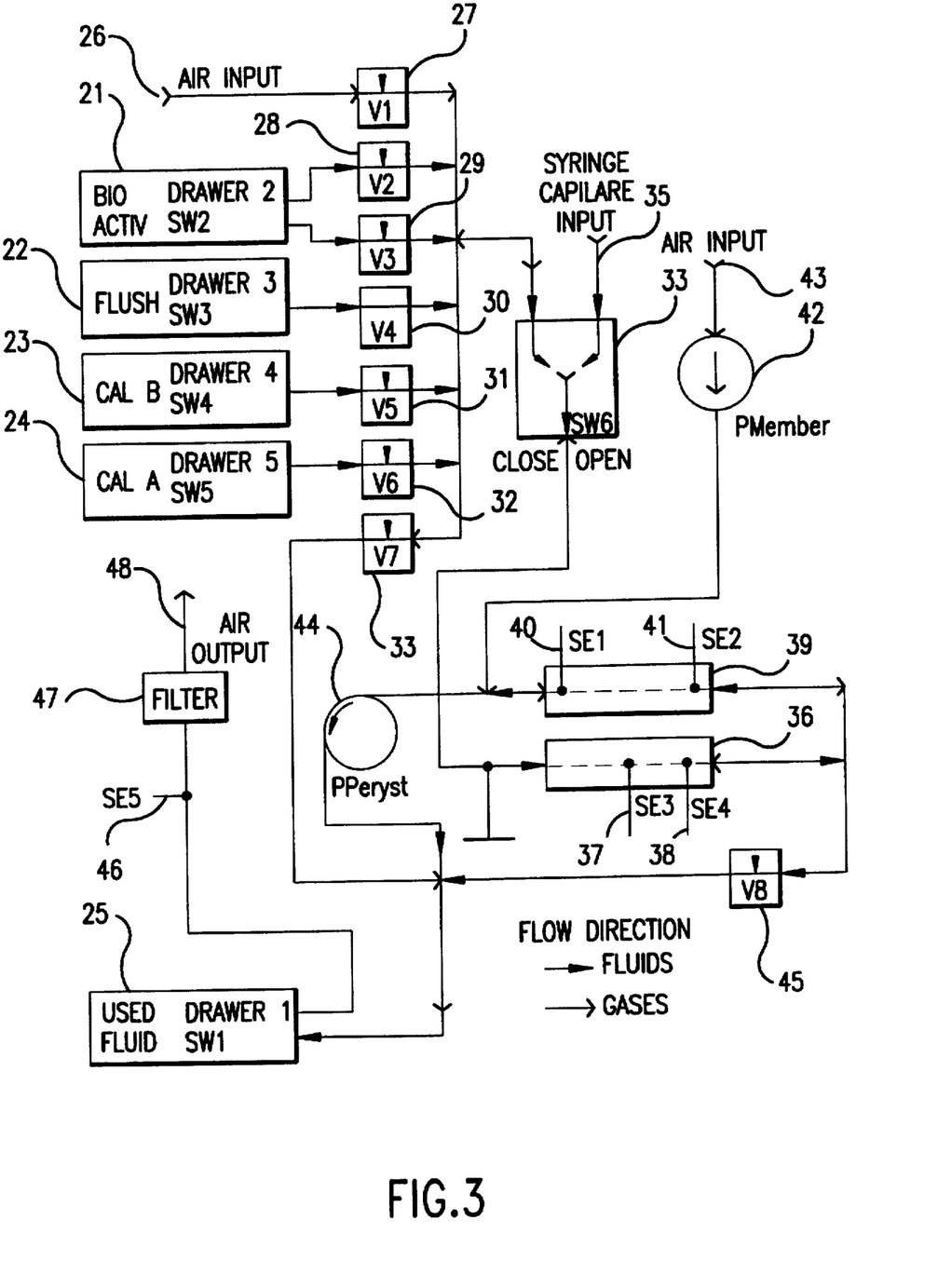
FIG. 3 shows a schematic of the gas-hydraulic system of the analyzer with two separated measuring channels.
Figure 4:
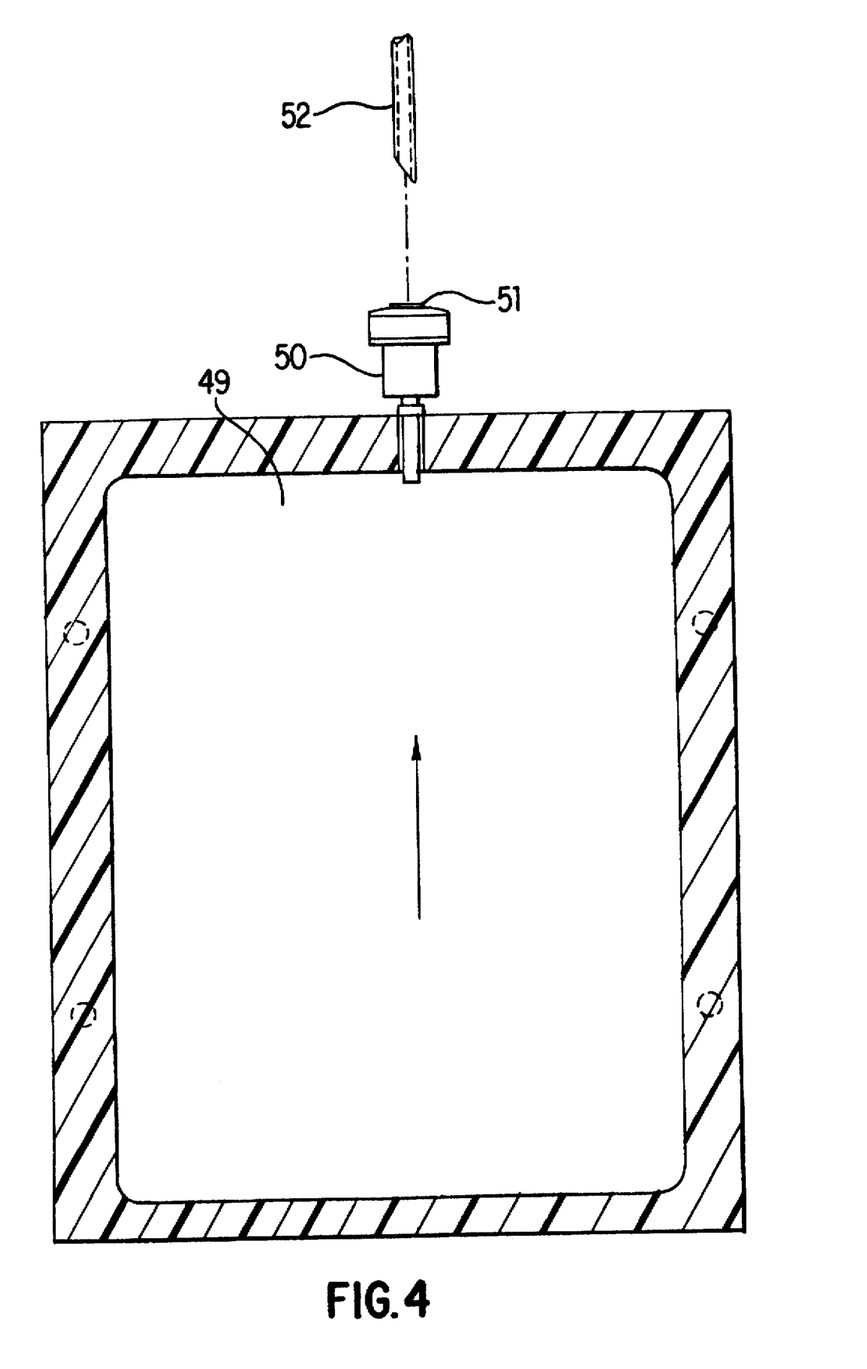
FIG. 4 shows an elastic, gas-impermeable container in accordance with the invention.

The gas-hydraulic system of the analyzer 1, as shown in the block diagram of FIG. 3, comprises a series of drawers 21, 22, 23 and 24 assigned for the exchangeable bags containing fluids saturated with the calibrating gases and the working fluids. The replacement of bags is carried out "dry" by pulling open the drawer containing the given agent, taking out the old emptied bag, inserting a new bag and, after having read out the bar code by the light pen 6, shutting the drawer by inserting a ferrule with a needle in the plug of the fastened bag, the plug being made of self-tightening rubber typical for closures of vials from which medicine is drawn with a syringe. The drawer 25 with a container for the used fluids is designed also in a similar way. FIG. 4 illustrates an elastic, gas-impermeable container which comprises a bag 49, a connector 50 with a plug 51 and a needle of the ferrule 52 which is implanted into the plug 51 of the connector 50.

The contents of bags placed in the drawers 21, 22, 23 and 24, as well as the air from the inlet clamp 26 for air, are fed via valves 27, 28, 29, 30, 31 and 32 into a hydraulic switch 33 and via the next valve 34, optionally included in the measuring cycle, to the drawer 25 with a container for the used fluid. The sample under testing is fed to the second inlet of the hydraulic switch 33. The outlet of the hydraulic switch 33 is connected with the measuring chamber comprising the first measuring channel 36 via a block for measuring the acid-base equilibrium and a block for measuring ions with the measuring electrodes 37 and 38, as well as a second measuring channel 39 comprising only a block for measuring the acid-base equilibrium with the measuring electrodes 40 and 41. The outlet of the measuring chamber is connected via a membrane pump 42 to the second inlet clamp 43 for air, used also for taking the oxygen from air, and to a peristaltic pump 44. The outlet of the first measuring channel 36 via the next valve 45, and the outlet of the peristaltic pump 44, are connected with the drawer 25 comprising a container for the used fluid. The drawer 25 with a container for the used fluid is connected by a hydraulic line containing the next electrode 46 with a filter 47. The outlet of the filter 47 is connected with the outlet clamp 48 for air.

The operating elements of the analyzer 1, such as the valves 27, 28, 29, 30, 31, 32, 34 and 45, the hydraulic switch 33 and the pumps 42 and 44, all of which are shown in FIG. 3, are controlled by the control module 13 from the computer. The arrows indicate the flow direction of fluids and gases. The oxygen electrode presented in FIG. 5 comprises a casting 53 made of insulating material in which an electrode set 54 and a pin set 55 are placed. The electrode set 54 is made of a cathode 56, placed in the glass casting 57 and an anode 58, both electrodes being placed in a cup 59 with electrolyte 60. A membrane 62 tightened with a packing ring 63 is put over the electrode set 54 from the side of the measuring chamber 61. On the other side the electrode set 54 is tightened with a packing 64 and through the cup 59 pressed down by a nut 65. The whole thing being covered with a filling compound 66. The cathode 57 and the anode 58 are connected with conduits 67, 68 with the contacts of the pin set 55.

Figure 5:
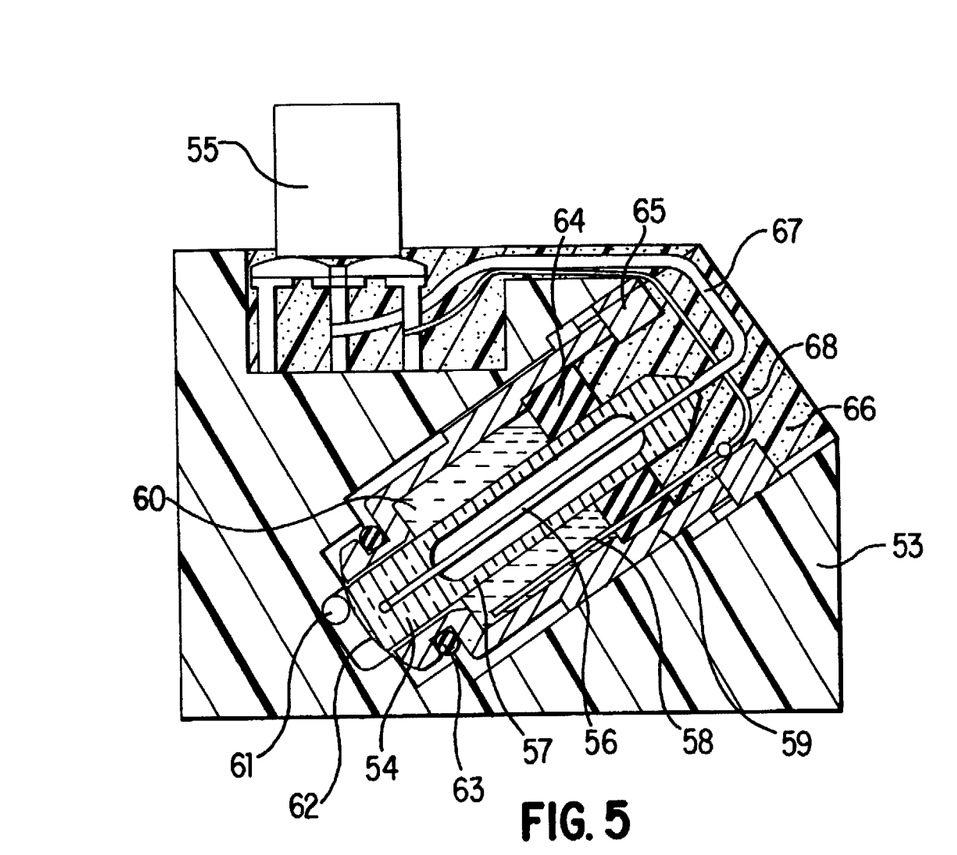
FIG. 5 shows an oxygen electrode according to the invention.

In the oxygen electrode, the construction of which is shown in FIG. 5 the cathodes and anodes were used according to the below-mentioned examples.

Example 1: The anode made of silver wire covered with a silver chloride: the cathode made of gold wire. This solution is known from the prior art and is presented for a comparative reason.

Example 2: The anode made of tungstic wire; the cathode made of gold wire.

Example 3: The anode made of tungstic wire; the cathode made of platinum wire.

Example 4: The anode made of molybdenum wire; the cathode made of platinum wire.

In all the examples, the diameter of the silver, tungstic and molybdenum wires was 0.25 µm while the diameter of the gold and platinum wires was 25 µm. The electrolyte being a phosphorus buffer with a pH equal 7, and in example 1 additionally contained potassium chloride of a concentration of 0.1 mole per liter.

Figure 6:
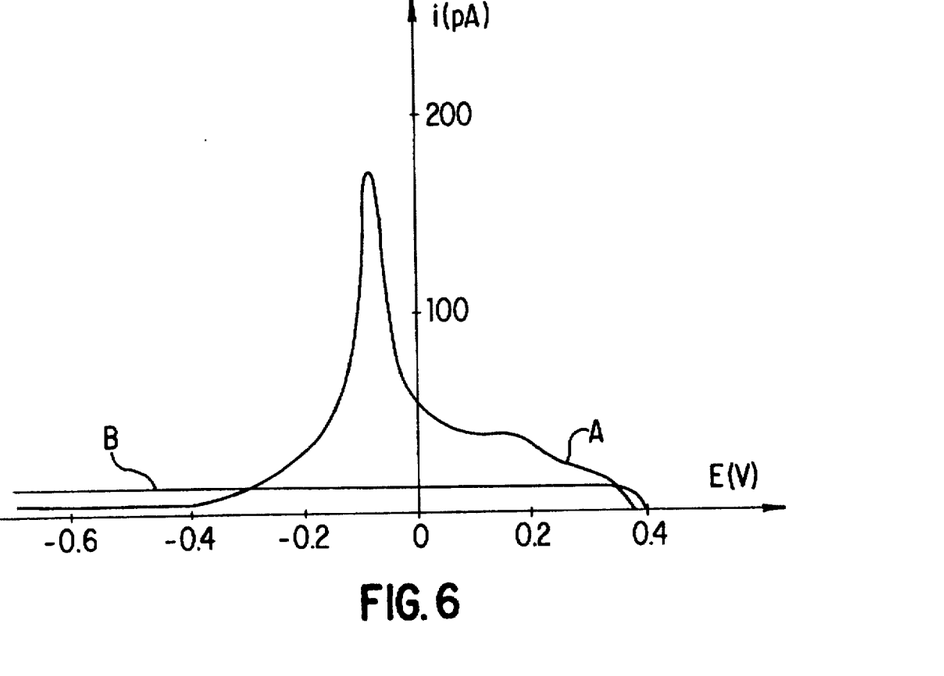
FIG. 6 is a diagram of a voltametric electrode curve.

In examples 1 and 2, voltametric curves were registered in gas not comprising oxygen and with potentials ranging from −0.7 V to +0.4 V and with the speed of polarization changes of 0.1 V/s. In example 1, after one week of maintaining the electrode at working potential of −0.7 V in the atmospheric oxygen, a high peak of current was registered on the voltametric curves, with a potential of about −0.1 V, resulting from the oxidation of the silver deposited on the cathode made of gold which shows the curve A in FIG. 2. That example presents a solution known from the prior art. In the analogical conditions for the electrode according to example 2, after three months of working, the registered course of the voltametric curve indicated lack of substance electrochemically active on the cathode material curve B, FIG. 6.

Figure 7:
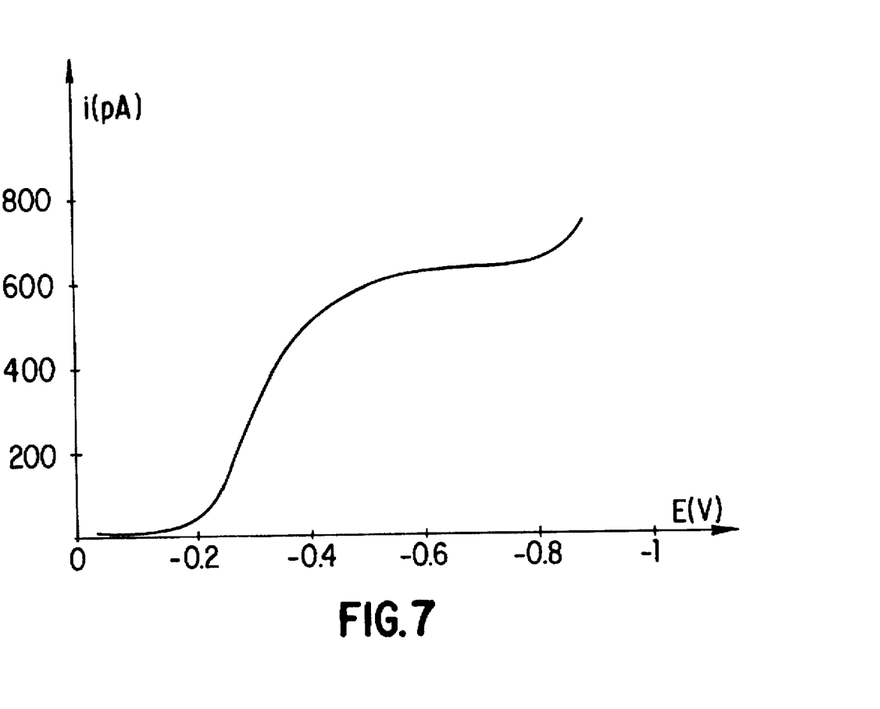
FIG. 7 is a diagram of a polarographic reduction of oxygen for the electrode curve of FIG. 6.

The electrodes from according to examples 3 and 4 were used for measuring atmospheric oxygen during the period of three months. They showed a great stability of the measured current of about +1% and a very little zero current of below 5 pA. Simultaneously, during all that period of time, the electrode was revealing linear characteristics of dependence of the measured current from the partial pressure of °2 ranging from 0 to 100% of the °2 contents. A typical polarographic curve of oxygen reduction for those electrodes is presented in FIG. 7. The electrode according to example 1 measured in the same conditions, after four weeks of working gave unstable measurement results, the zero current exceeded 10 pA while in case of oxygen measurements more than 50% showed non-linear curve of dependency of the measured current from the partial pressure.

The oxygen electrode made according to the invention gives stable measurements of the partial pressure of °2 for a long period of time, for instance, during six months, without a necessity of its disassembling from the measuring device and without a necessity of carrying out any conservation treatments.

The oxygen electrode according to the invention finds its application in a constant monitoring of partial pressure of °2 for a long period of time in the artificial-respiratory apparatus, in blood analyzers, at heart surgeries, in anesthesia, in incubators, at the evaluation of the strength and fitness tests, in the fermentation industry, for control of a course of enzymatic reactions, for control of a combustion process and in other cases. It may be used as a dipping electrode, en electrode for measurement in gases, a flow electrode or an electrode intended to be introduced into a live tissue. Moreover the solution according to the invention may be applied in enzymatic amperometric electrodes equipped with a membrane comprising an immobilized enzyme, for example, for glucose marking.

In the device according to the invention, samples of the fluid under test, of the calibrating fluids, and of the working fluids (e.g. the rinsing fluids), are passed through the measuring chamber 15 in time intervals controlled by the control unit 4 for measuring the parameters of a sample of fluid. Standard aqueous solutions saturated with gases are used as calibrating fluids, while the oxygen is drawn from air.

Next, all the fluids are divided, according to the measuring cycle, between the two measuring channels, the first 36 and the second 39, and their physico-chemical properties are determined by means of the measuring electrodes placed in the channels 36 and 39. The results of the measurements for each measuring channel are recalculated in a common electronic system, in this case in the computer.

The illustrated embodiments were chosen and described in order to best explain the principles of the invention and its practical application to thereby enable others skilled in the art to best utilize the invention and various embodiments and with various modifications as are suited to the particular use contemplated. It is intended that the scope of the invention only be limited by the claims appended hereto.

We claim:

1. A closed container for holding calibrating fluids with a specified pH or partial pressure of gas as a reference in liquid analysis device for measuring parameters of a sample of fluid, comprising:

an elastic, impermeable thick-wall or barrier type of bag enclosure for containing gases within an aqueous solution, said container having a fluid flow outlet connecting element;

wherein said connecting element is a self-tightening elastic joint comprising rubber materials, said self-tightening elastic joints ensuring tightness of a connection between the container and the device, said joint remaining closed during filling, storing, installing and using of the container in the device, whereby the calibrating fluids maintain a constant concentration of saturating gases within said solution during storage, installation and use of the container.

2. An oxygen electrode in a liquid analysis device for measuring parameters of a sample of fluid, comprising:

a Clark's electrode system;

wherein an anode of the electrode system is made of an element selected from the VIB group of the periodic table system of chemical elements, where said measured parameters include pH or partial pressure of gas components in said fluid.

3. The oxygen electrode according to claim 2, wherein said anode is made of tungsten.

4. The oxygen electrode according to claim 2, wherein said anode is made of molybdenum.

5. A liquid analysis device for measuring parameters of a sample of fluid, comprising:

an analyzer and a control unit with a monitor, the analyzer comprising a measuring chamber with measuring electrodes, the measuring chamber being connected with closed, replaceable containers for holding calibrating fluids with a specified pH or partial pressure of gas as a reference and for holding working fluids and into which measuring chamber are introduced a sample of a measured fluid, control elements and operating elements to control the operation of the device and to maintain a constant temperature of the device, as well as computer processing elements for transforming results of measurements into quantities of parameters of the sample of fluid;

wherein the device comprises elastic, impermeable, and exchangeable containers for the calibrating fluids, said containers having a connecting element wherein said connecting element is a self-tightening elastic joint comprising rubber materials, said self-tightening elastic joint ensuring tightness of a connection between the container and the device, said joint remaining closed during filling, storing, installing and using of the container in the device, whereby the calibrating fluids maintain a constant concentration of saturating gases during storage, installation and use of the container.

6. A liquid analysis device for measuring parameters of a sample of fluid, comprising:

an analyzer and a control unit with a monitor, the analyzer comprising a measuring chamber with measuring electrodes, the measuring chamber being connected with closed, replaceable containers for holding calibrating fluids with a specified pH or partial pressure of gas as a reference and for holding working fluids and into which measuring chamber are introduced a sample of a measured fluid, control elements and operating elements to control the operation of the device and to maintain a constant temperature of the device, as well as computer processing elements for transforming results of measurements into quantities of parameters of the sample of fluid;

wherein the device comprises elastic, impermeable, and exchangeable containers for the calibrating fluids, said containers having a connecting element wherein said connecting element is a self-tightening elastic joint ensuring tightness of a connection between the container and the device, said joint remaining closed during filling, storing, installing and using of the container in the device, whereby the calibrating fluids maintain a constant concentration of saturating gases during storage, installation and use of the container; and further comprising oxygen electrodes each comprising a Clark's electrode system, wherein an anode of the electrode system is made of an element selected from the VIB group of the periodic table system of chemical elements.

7. The device according to claim 6, wherein said anode is made of tungsten.

8. The device according to claim 6, wherein said anode is made of molybdenum.

9. The device according to claim 5, wherein said measuring chamber comprises at least two measuring channels with measuring electrodes for measuring an acid-base equilibrium state in said fluid sample, said measuring electrodes included in each of the measuring channels of the equipment and connected with common electronic systems.

10. A liquid analysis method for measuring parameters of a sample of fluid, comprising the steps of:

passing samples of a measured fluid, a calibrating fluid and a working fluid through a measuring chamber having at least two distinct and independent measuring channels at specified intervals of time as performed alternately and sequentially according to pre-planned steps in a proportional time-allocated measuring cycle;

measuring physical-chemical properties of the measured fluid and of the calibrating fluids with sets of measuring electrodes;

determining quantities of parameters of a sample of fluid on the basis of the measured properties;

introducing standard aqueous solutions saturated with gases as well as oxygen taken from air as calibrating fluids for exposure to the measuring electrodes in the measuring chamber;

dividing the calibrating fluid standard solutions alternatively with the measured sample of fluid and with the working fluids and in accordance with the measuring cycle among said at least two distinct and independent measuring channels disposed in the measuring chamber, each channel comprising a set of measuring electrodes for determining an acid-base equilibrium state in said fluid sample; and recalculating measurement results for each measuring channel in a common electronic system.

* * * * *